(12) United States Patent
Camenzind et al.

(10) Patent No.: US 6,362,138 B1
(45) Date of Patent: *Mar. 26, 2002

(54) HETEROCYCLIC THIOETHERS AS ADDITIVES FOR LUBRICANTS

(75) Inventors: Hugo Camenzind, Bern; Samuel Evans, Marly; Alfred Dratva, Bottmingen; Peter Hänggi, Giffers, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/663,822

(22) Filed: Sep. 15, 2000

Related U.S. Application Data

(63) Continuation of application No. 09/128,086, filed on Aug. 3, 1998, now Pat. No. 6,150,307.

(30) Foreign Application Priority Data

Aug. 6, 1997 (CH) .............................. 1863/97

(51) Int. Cl.[7] .................. C10M 135/36; C07D 285/125; C07D 277/74
(52) U.S. Cl. ..................... 508/273; 508/274; 508/275; 548/142; 548/169; 548/170; 548/171
(58) Field of Search ................ 508/273, 274, 508/275; 548/142, 169, 170, 171

(56) References Cited

U.S. PATENT DOCUMENTS

| | | | |
|---|---|---|---|
| 3,455,676 A | 7/1969 | Ayad | 71/90 |
| 3,591,475 A | 7/1971 | Griesbaum et al. | 204/158 R |
| 3,639,663 A | 2/1972 | Ayad | 260/306 |
| 5,051,198 A | 9/1991 | Salomon | 252/47 |
| 5,258,258 A | 11/1993 | Matsubara et al. | 430/204 |
| 5,618,778 A | 4/1997 | Wirth et al. | 508/274 |
| 5,686,397 A | 11/1997 | Baranski et al. | 508/274 |

FOREIGN PATENT DOCUMENTS

| | | |
|---|---|---|
| EP | 0191948 | 8/1986 |
| GB | 1044147 | 9/1966 |

OTHER PUBLICATIONS

Prilezhaeva et al, "Syntheses on the Basis of 2–Benzothiazolyvinyl Sulfide", (1965), pp. 1847–1853.
Chem Abstracts vol. 117, No. 26, 261734k (1992).
Chem. Abstracts vol. 119, No. 8, 82821f (1993).
Chem. Abstracts vol. 113, No. 21, 191360b (1990).
Chem. Abstracts vol. 88, No. 13, 89573b (1978).
Chem. Abstracts vol. 94, No. 5, 30614m, (1981).
Chem. Abstracts vol. 66, 55430h, Prilezhaeva et al., Syntheses based on 2–benzothiazolyl vinyl Sulfide (1967).
Chem. Abstracts. vol. 122, 68345 Takada et al., Processing solution for direct offset printing using silver salt diffusion transfer method (1995).
Chem. Abstracts. vol. 94, No. 5, 30614m, (1981).

*Primary Examiner*—Jerry D. Johnson
(74) *Attorney, Agent, or Firm*—Kevin T. Mansfield

(57) ABSTRACT

This invention relates to compounds which are suitable as ash-free antiwear additives and antioxidants, to lubricant compositions comprising said compounds as well as to their use.

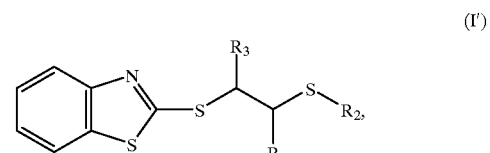

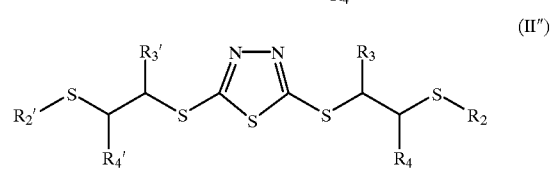

are particularly preferred.

In the preferred compounds I',
  $R_2$ is isooctyloxycarbonylmethyl, $R_3$ is isooctyloxycarbonylmethylthiomethyl and $R_4$ is hydrogen; or
  $R_2$ is tert-nonyl and $R_3$ is tert-nonylthiomethyl and $R_4$ is hydrogen; or
  $R_2$ is isooctyloxycarbonylmethyl, $R_3$ is hydrogen and $R_4$ is isooctyloxycarbonylmethylthiomethyl; or
  $R_2$ is tert-nonyl, $R_3$ is hydrogen and $R_4$ I is tert-nonylthiomethyl.

In the preferred compounds II',
  $R_2$ and $R_2$' are isooctyloxycarbonylmethyl, $R_3$ and $R_3$' are isooctyloxycarbonylmethylthiomethyl and $R_4$ and $R_4$' are hydrogen; or
  $R_2$ and $R_2$' are tert-nonyl, $R_3$ and $R_3$' are tert-nonylthiomethyl and $R_4$ and $R_4$' are hydrogen; or
  $R_2$ and $R_2$' are isooctyloxycarbonylmethyl, $R_3$ and $R_3$' are hydrogen and $R_4$ and $R_4$' are isooctyloxycarbonylmethylthio; or
  $R_2$ and $R_2$' are tert-nonyl, $R_3$ and $R_3$' are hydrogen and $R_4$ and $R_4$' are tert-nonylthiomethyl.

12 Claims, No Drawings

HETEROCYCLIC THIOETHERS AS ADDITIVES FOR LUBRICANTS

This application is a continuation of U.S. Ser. No. 09/128,086, filed Aug. 3, 1998, now U.S. Pat. No. 6,150,307.

The present invention relates to compounds of formulae I and II, which are suitable as ash-free antiwear additives and antioxidants, to lubricant compositions comprising compounds of formulae I and II as well as to their use.

For operating combustion engines, it is necessary to use lubricants having a low metal content and, therefore, a low ash content and, in view of exhaust gas catalyst compatibility, also a low phosphorus content. This invention therefore has for its object to provide metal-free and phosphorus-free additives or additive combinations which approach the good antioxidative and wear protection of the zinc dialkyldithiophosphates used to date.

U.S. Pat. No. 3,591,475 describes the preparation of asymmetrical dithioethers of the general formula

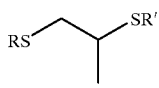

by addition of a mercaptan R'SH to an allyl sulfide (RS—CH$_2$CH=CH$_2$). The definitions of R and R' include numerous substituents of different structures. There is no description given of a dithioether containing a heterocyclic radical as a defined single compound. Benzothiazolyl is only mentioned as an example in the sense of an enumeration. The use of the compounds described in U.S. Pat. No. 3,591,475 is also disclosed unspecifically. Their suitability as agrochemicals having antiparasitic properties is mentioned there. In addition, these compounds are said to be suitable as stabilisers for polyolefins and also as additives for lubricants.

The preparation of benzothiazolyl dithioethers of formula

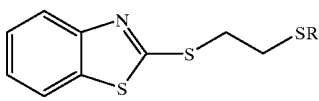

(R = Et, tert-but., phenyl, Et$_2$OH, acetyl)

with herbicidal activity is described on page 1847 of the English translation of *Syntheses on the Basis of 2-benzothiazolylvinyl Sulfide, Zhurnal Organicheskoi Khimii*, Vol. 2, No. 10, pp. 1883–1891, October 1966.

U.S. Pat. No. 5,258,258 describes processing solutions for the development of lithographic printing plates, which comprise thiadiazolyl dithioethers of formula

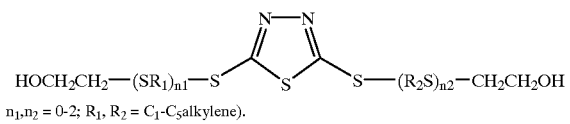

n$_1$,n$_2$ = 0-2; R$_1$, R$_2$ = C$_1$-C$_5$alkylene).

U.S. Pat. No. 5,051,198 describes reaction products which are obtainable by reacting mercaptans with β-thiodialkanols. These reaction products can be used as antioxidants.

This invention relates to compounds of formulae I and II described hereinafter, which are suitable as improved ash- and phosphorus-free antiwear additives and which additionally have an antioxidative effect:

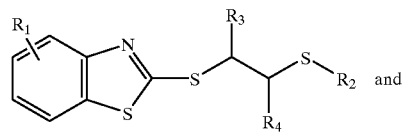

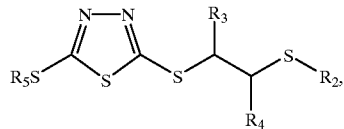

wherein
R$_1$ is hydrogen or C$_1$-C$_{20}$alkyl;
R$_2$ is a substituent from the group consisting of C$_1$-C$_{20}$alkyl, C$_5$-C$_{12}$cycloalkyl, C$_7$-C$_{12}$bicycloalkyl, phenyl, C$_7$-C$_{18}$alkylphenyl, naphthyl and C$_7$-C$_9$phenylalkyl, which substituent may be substituted by one or more than one substituent from the group consisting of amino, carboxy and hydroxy and/or may be interrupted by one or more than one bivalent radical from the group consisting of —O—, —NR$_6$—, —C(=O)—O—, —O—C(=O)—, —C(=O)—NR$_6$— and —NR$_6$—C(=O)—;
R$_3$ and R$_4$ are hydrogen or have the meanings of R$_2$, with the proviso that R$_2$ is C$_4$-C$_{20}$alkyl if R$_3$ and R$_4$ are hydrogen;
R$_5$ is hydrogen or groups of the partial formula

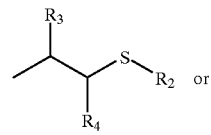

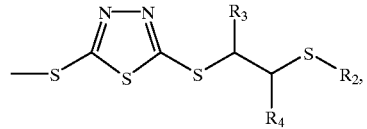

wherein R$_2$, R$_3$ and R$_4$ have the cited meanings or have the meaning of R$_2$;
and R$_6$ is hydrogen or C$_1$-C$_4$alkyl.

The compounds of formulae I and II are particularly suitable as multifunctional antiwear additives with additional antioxidative effect for lubricants, gear oils, hydraulic and metal working fluids as well as for greases. They are substantially ash- and phosphorus-free.

The definitions and terms used within the scope of the description of this invention preferably have the following meanings:

Examples of C$_1$-C$_{20}$alkyl are methyl, ethyl, n- or isopropyl or n-, sec- or tert-butyl and also straight-chain or branched pentyl, hexyl, heptyl, octyl, nonyl, decyl, undecyl or dodecyl, typically isooctyl or tert-nonyl. Examples of C$_5$-C$_{12}$cycloalkyl are cyclopentyl or cyclohexyl. Examples of C$_7$-C$_{12}$bicycloalkyl are e.g. bornyl or norbornyl. Examples of C$_7$-C$_{18}$alkylphenyl are phenyl which is substituted by mono-, di- or trimethyl. Examples of C$_7$-C$_9$phenylalkyl are e.g. benzyl or 2-phenylethyl.

In another of its aspects, this invention also relates to compounds of formulae I and II including all cases of isomerism, for example bond isomers or stereoisomers, resulting from the presence of a chiral centre. These cases of isomerism encompass optically pure enantiomers, diastereomers as well as racemic mixtures.

Preferred compounds are those of formulae I and II described above, wherein $R_1$ is hydrogen; $R_2$ is a substituent from the group consisting of $C_1$–$C_{20}$alkyl, phenyl, $C_7$–$C_{18}$-alkylphenyl and $C_7$–$C_9$phenylalkyl, which substituent may be substituted by one or more than one substituent from the group consisting of amino, carboxy and hydroxy and/or may be interrupted by one or more than one bivalent radical from the group consisting of —O—, —NR$_6$—, —C(=O)—O—, —O—C(=O)—, —C(=O)—NR$_6$— and —NR$_6$—C(=O)—;

$R_3$ and $R_4$ are hydrogen or have the meaning of $R_2$, with the proviso that $R_2$ is $C_4$–$C_{20}$alkyl if $R_3$ and $R_4$ are hydrogen;

$R_5$ has the meanings of $R_2$ or is groups of the partial formulae (A) and (B), wherein $R_2$, $R_3$ and $R_4$ have the cited meanings; and $R_6$ is hydrogen or alkyl.

Particularly preferred compounds are those of formulae I and II, wherein $R_1$ is hydrogen; $R_2$ is a substituent from the group consisting of $C_1$–$C_{20}$alkyl, phenyl, $C_7$–$C_{18}$-alkylphenyl and $C_7$–$C_9$phenylalkyl, which substituent may be interrupted by one or more than one bivalent radical from the group consisting of —O—, —C(=O)—O— and —O—C(=O)—;

$R_3$ and $R_4$ are hydrogen or have the meanings of $R_2$, with the proviso that $R_2$ is $C_4$–$C_{20}$alkyl if $R_3$ and $R_4$ are hydrogen;

$R_5$ has the meanings of $R_2$ or is groups of the partial formulae (A) and (B), wherein $R_2$, $R_3$ and $R_4$ have the cited meanings.

Very particularly preferred objects of this invention are compounds of formulae I and II, wherein $R_1$ is hydrogen; $R_2$ is $C_1$–$C_{20}$alkyl which may be interrupted by a bivalent radical from the group consisting of —O—, —C(=O)—O— and —O—C(=O)—;

$R_3$ and $R_4$ are hydrogen or have the meanings of $R_2$, with the proviso that $R_2$ is $C_{4-C20}$alkyl if $R_3$ and $R_4$ are hydrogen;

$R_5$ has the meanings of $R_2$ or is groups of the partial formulae (A) and (B), wherein $R_2$, $R_3$ and $R_4$ have the cited meanings.

Particularly preferred compounds are those of formula

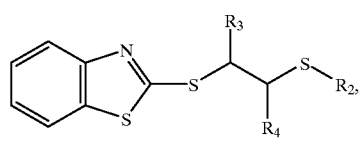

(I')

wherein $R_2$ is $C_4$–$C_{18}$alkoxycarbonylmethyl, $R_3$ is $C_4$–$C_{18}$alkoxycarbonylmethylthiomethyl and $R_4$ is hydrogen; or $R_2$ is $C_5$–$C_{12}$alkyl, $R_3$ is $C_5$–$C_{12}$alkylthiomethyl and $R_4$ is hydrogen; or $R_2$ is $C_4$–$C_{18}$alkoxycarbonylmethyl, $R_3$ is hydrogen and $R_4$ is $C_4$–$C_{18}$alkoxycarbonylmethylthiomethyl; or $R_2$ is $C_5$–$C_{12}$alkyl, $R_3$ is hydrogen and $R_4$ is $C_5$–$C_{12}$alkylthiomethyl, and compounds of formula:

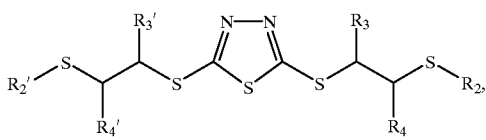

(II')

wherein $R_2$ and $R_2$' are $C_4$–$C_{18}$alkoxycarbonylmethyl, $R_3$ and $R_3$' are $C_4$–$C_{18}$alkoxycarbonylmethylthiomethyl, and $R_4$ and $R_4$' are hydrogen; or $R_2$ and $R_2$' are $C_5$–$C_{12}$alkyl, $R_3$ and $R_3$' are $C_5$–$C_{12}$alkylthiomethyl and $R_4$ and $R_4$' are hydrogen; or $R_2$ and $R_2$' are $C_4$–$C_{18}$alkoxycarbonylmethyl, $R_3$ and $R_3$' hydrogen and $R_4$ and $R_4$' are $C_4$–$C_{18}$alkoxycarbonylmethylthiomethyl; or $R_2$ and $R_2$' are $C_5$–$C_{12}$alkyl, $R_3$ and $R_3$' are hydrogen and $R_4$ and $R_4$' are $C_5$–$C_{12}$alkylthiomethyl.

Especially preferred are compounds of formula I', wherein $R_2$ is isooctyloxycarbonylmethyl, $R_3$ is isooctyloxycarbonylmethylthiomethyl and $R_4$ is hydrogen; or $R_2$ is tert-nonyl, $R_3$ is tert-nonylthiomethyl and $R_4$ is hydrogen; or $R_2$ is isooctyloxycarbonylmethyl, $R_3$ is hydrogen and $R_4$ is isooctyloxycarbonylmethylthiomethyl; or $R_2$ is tert-nonyl, $R_3$ is hydrogen and $R_4$ is tert-nonylthiomethyl, and also compounds of formula II', wherein $R_2$ and $R_2$' are isooctyloxycarbonylmethyl, $R_3$ and $R_3$' are isooctyloxycarbonylmethylthiomethyl and $R_4$ and $R_4$' are hydrogen; or $R_2$ and $R_2$' are tert-nonyl, $R_3$ and $R_3$' are tert-nonylthiomethyl and $R_4$ and $R_4$' are hydrogen; or $R_2$ and $R_2$' are $C_5$–$C_{10}$isooctyloxycarbonylmethyl, $R_3$ and $R_3$' are hydrogen and $R_4$ and $R_4$' are isooctyloxycarbonylmethyl; or $R_2$ and $R_2$' are $C_5$–$C_{10}$tert-nonyl, $R_3$ and $R_3$' are hydrogen and $R_4$ and $R_4$' are tert-nonylthiomethyl.

This invention furthermore relates to compositions with lubricants comprising a compound of formula I or II or mixtures thereof in combination with a base oil of lubricating viscosity or with fuels.

This invention also relates to a process for improving the performance properties of lubricants or lubricating greases, such as motor oil, turbine oil, gear oil, hydraulic or metal working fluids or liquid fuels, e.g. diesel or carburettor fuels, which comprises adding at least one compound of formula I or II to achieve a friction-reducing and/or antioxidative effect. Accordingly, this invention also relates to the use of compounds of formula I or II as additives in lubricants or lubricating greases, such as motor oils, turbine oils, gear oils, hydraulic fluids, metal working fluids, lubricating greases or diesel or carburettor fuels.

A base oil of lubricating viscosity can be used for the preparation of lubricating greases or lubricants, metal working, gear or hydraulic fluids.

Such lubricating greases or lubricants, metal working, gear and hydraulic fluids are based, for example, on mineral or synthetic lubricants or oils or on mixtures thereof. The skilled person is familiar with them, and they are described in the relevant literature, for example in *Chemistry and Technology of Lubricants;* Mortier, R. M. and Orszulik, S. T. (Editors); 1992 Blackie and Son Ltd. for GB, VCH-Publishers N. Y. for U.S., ISBN 0-216-92921-0, see pages 208 et seq. and 269 et seq.; in *Kirk-Othmer Encyclopedia of Chemical Technology,* fourth Edition 1969, J. Wiley & Sons, New York, Vol. 13, page 533 et seq. (Hydraulic Fluids); *Performance Testing of Hydraulic Fluids;* R. Tourret and E. P. Wright, Hyden & Son Ltd. GB, on behalf of The Institute of Petroleum London, ISBN 0 85501 317 6; *Ullmann's Encyclopedia of Ind. Chem.,* Fifth Completely revised Edition, *Verlag Chemie,* DE-Weinheim, VCH-Publishers for U.S., Vol. A 15, page 423 et seq. (lubricants), Vol. A 13, page 165 et seq. (hydraulic fluids).

The lubricants are preferably oils and greases, based e.g. on a mineral oil. Oils are preferred.

Another group of lubricants which may be used are vegetable or animal oils, fats, tallows and waxes or their mixtures with each other or their mixtures with the mentioned mineral or synthetic oils. Vegetable and animal oils, fats, tallows and waxes are, for example, palmnut oil, palm oil, olive oil, beet oil, rapeseed oil, linseed oil, groundnut oil, soybean oil, cottonseed oil, sunflower oil, pumpkin seed oil, coconut oil, corn oil, castor oil, walnut oil and mixtures thereof, fish oils, tallows of slaughter animals, such as beef tallow, neat's foot oil and bone fat as well as their modified epoxidised and sulfoxidised forms, for example epoxidised soybean oil.

Examples of synthetic lubricants include lubricants based on aliphatic or aromatic carboxylates, polymeric esters, polyalkylene oxides, phosphates, poly-α-olefins or silicones, on a diester of divalent acids with a monovalent alcohol, e.g. dioctyl sebacate or dinonyl adipate, on a triester of trimethylolpropane with a monovalent acid or with a mixture of such acids, e.g. trimethylolpropane tripelargonate, trimethylolpropane tricaprylate or mixtures thereof, on a tetraester of pentaerythritol with a monovalent acid or with a mixture of such acids, e.g. pentaerythritol tetracaprylate, or on a complex ester of monovalent and divalent acids with polyvalent alcohols, for example a complex ester of trimethylolpropane with caprylic and sebacic acid or of a mixture thereof. Particularly suitable are, besides mineral oils, e.g. poly-α-olefins, ester-based lubricants, phosphates, glycols, polyglycols and polyalkylene glycols and their mixtures with water.

Metal working fluids and hydraulic fluids can be prepared on the basis of the same substances as those described above for the lubricants. They are often also emulsions of such substances with water or other liquids.

The lubricant compositions of this invention are used, for example in combustion engines, e.g. in motor vehicles equipped e.g. with engines of the Otto, diesel, two-stroke, Wankel or orbital type.

The compounds of formula I or II are readily soluble in lubricants, in metal working and hydraulic fluids and are therefore particularly suitable as additives for lubricants, metal working and hydraulic fluids.

The compositions expediently comprise 0.005 up to 10.0% by weight of the compounds of formula I or II, preferably 0.01–5.0% by weight, more preferably 0.01–0.9% weight.

The compounds of formula I or II can be admixed to the lubricants in a manner known per se. The compounds are readily soluble for example in oleophilic solvents, e.g. in oils. They can also be used together with additional additives to prepare a concentrate or a so-called additive packet which, depending on the consumption, can be diluted to the concentrations to be used for the corresponding lubricant.

The lubricants, metal working and hydraulic fluids can additionally contain further additives which are added to further improve their basic properties. These additives include: additional antioxidants, metal passivators, rust inhibitors, viscosity index improvers, pour point depressants, dispersants, detergents, other extreme pressure additives, antiwear additives and friction reducers. Where appropriate, these additives can act synergistically with each other or with the novel compounds. Such additives are added in the usual amounts ranging from about 0.01 to 10.0% by weight each. Should it still be necessary to add phosphorus- or metal-containing additives, then these additives are preferably added in small amounts, for example of about 0.01 to 0.5% by weight.

Examples of further additives are:
Examples of phenolic antioxidants:

1.1 Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(a-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2 Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3 Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tertbutyl-4-hydroxyanisole, 3,5-di-tert-butyl-4-hydroxyphenyl stearate, bis(3,5-di-tert-butyl-4-hydroxyphenyl) adipate.

1.4 Tocopherols, α-, β-, γ-, δ-tocopherol and mixtures thereof (vitamin E).

1.5 Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6 Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis-(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy2-methylphenyl)-4-n-dodecylmercaptobutane, 1,1,5,5-tetra(5-tert-butyl-4-hydroxy-2-methylphenyl) pentane.

1.7 O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3, 5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8 Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9 Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10 Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)-isocyanurate.

1.11 Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12 Acylaminophenols, for example 4-hydroxylauranilide, 4-hydroxystearanilide, octyl N-(3,5-di-tert-butyl-4-hydroxyphenyl)carbamate.

1.13 Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14 Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis (hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16 Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17 Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine, N,N'-bis(3,5-di-tert-butyl-4-hydroxyphenylpropionyl)-hydrazine.

1.18. Ascorbic acid (vitamin C)

1.19. Aminic antioxidants: for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyl-diphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazine, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin4-ol.

Examples of other antioxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators, for example for copper, are:
a) Benzotriazoles and the derivatives thereof, for example 2-mercaptobenzotriazole, 2,5-dimercaptobenzotriazole, 4- or 5-alkylbenzotriazoles (e.g. tolutriazole) and the derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl) aminomethyl)tolutriazole and 1-[bis(2-ethylhexyl) aminomethyl)benzotriazole; and alkoxyalkylbenzotriazoles such as 1-(nonyloxymethyl) benzotriazole, 1-(1-butoxyethyl)benzotriazole and 1-(1-cyclohexyloxybutyl)tolutriazole.

b) 1,2,4-Triazoles and the derivatives thereof, for example 3-alkyl(or aryl)-1,2,4-triazoles, and Mannich bases of 1,2,4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles.

c) Imidazole derivatives, for example 4,4'-methylenebis(2-undecyl5-methylimidazole) and bis[(N-methyl)imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin- 2-one.

e) Amino compounds, for example salicylidenepropylenediamine, salicylaminoguanidine and the salts thereof.

Examples of rust inhibitors are:
a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-(2-carboxyethyl)-1-dodecyl-3-methylglycerol and the salts thereof, in particular the sodium salts and triethanolamine salts.

b) Nitrogen-containing compounds, for example:
   i. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.
   ii. Heterocyclic compounds, for example: substituted imidazolines and oxazolines, and 2-heptadecenyl-1-(2-hydroxyethyl)imidazoline.

c) Phosphorus-containing compounds, for example: Amine salts of phosphoric acid partial esters or phosphonic acid partial esters, and zinc dialkyldithiophosphates.

d) Sulfur-containing compounds, for example: barium dinonylnaphthalenesulfonates, calcium petroleum sulfonates, alkylthio-substituted aliphatic carboxylic acids, esters of aliphatic 2-sulfocarboxylic acids and the salts thereof.

e) Glycerol derivatives, for example: glycerol monooleate, 1-(alkylphenoxy)-3-(2-hydroxyethyl)glycerol, 1-(alkylphenoxy)-3-(2,3-dihydroxypropyl)glycerol and 2-carboxyalkyl-1,3-dialkylglycerol.

Examples of viscosity index improvers are:
Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are:
Poly(meth)acrylates, ethylene/vinyl acetate copolymer, alkyl polystyrenes, fumarate copolymers, alkylated naphthalene derivatives.

Examples of dispersants/surfactants are:
Polybutenylsuccinic amides or -imides, polybutenylphosphonic acid derivatives and basic magnesium, calcium and barium sulfonates and basic magnesium, calcium and barium phenolates.

Examples of extreme pressure and antiwear additives are:
Sulfur- and/or phosphorus- and/or halogen-containing compounds, for example chlorinated paraffins, sulfurised olefins or vegetable oils (soybean oil and rapeseed oil), alkyl- or aryl-di- or -trisulfides, zinc dialkyldithiophosphates, such as zinc-bis(2-ethylhexyl) dithiophosphate, zinc dithiocarbamates, such as zinc diamyldithiocarbamate, molybdenum phosphorodithioates, molybdenum dithiocarbamates, triarylphosphates, such as tripolyphosphate, tricresylphosphate, isopropyl phenylphosphate, amine salts of mono- or dialkylphosphoric acids, e.g. the amine salts of mono/di-hexylphosphate, amine salts of alkylphosphonic acids, such as the amine salt of methylphosphonic acid, triaryl phosphites, e.g. tris [nonylphenyl]phosphite, dialkyl phosphites, such as dioctyl phosphite, triaryl monothiophosphates, e.g. triphenyl thiophosphate or tris-[isononylphenyl]thionophosphate or tert-butylated triphenyl thionophosphates, substituted trialkyl mono- or dithiophosphates, for example [(diisopropoxyphosphinothioyl)thio]propionate or butylene-1,3-bis[(diisobutoxyphosphinothioyl)propionate], trithiophosphates, such as trithiophosphoric acid, S,S,S-tris (isooctyl-2-acetate), amine salts of 3-hydroxy-1,3-thiaphosphetane-3-oxide, benzotriazoles or the derivatives thereof, e.g. bis(2-ethylhexyl)aminomethyltolutriazole, dithiocarbamates, such as methylene-bis-dibutyldithiocarbamate, derivatives of 2-mercaptobenzothiazole, e.g. 1-[N,N-bis(2-ethylhexyl) amino-methyl]-2-mercapto-1H-1,3-benzothiazole, derivatives of 2,5-dimercapto-1,3,4-thiadiazole, such as 2,5-bis (tert-nonylditdithio)-1,3,4-thiadiazole.

Examples of frictional coefficient reducers are, for example, lard oil, oleic acid, tallow, rapeseed oil, sulfurised fats, amines. Other examples are cited in EP-A-565487.

Examples of special additives for use in water/oil metal working and hydraulic fluids are:
Emulsifiers: petroleum sulfonates, amines, such as polyethoxylated fatty amines, nonionic surface active substances; buffers: alkanolamines; biocides: triazines, thiazolinones, trisnitromethane, morpholine, sodium pyridene ethol; processing speed improvers: calcium sulfonates and barium sulfonates;

Examples of fuel additives:
Such additives are described in Kirk-Othmer, *Encyclopedia of Chemical Technology,* Vol. 12, 1994. They are mainly gasoline and diesel additives:

Gasoline: aminic antioxidants, in particular paraphenylenediamines, or phenolic antioxidants, e.g. 2,6-di-tert-butylphenol (as described above); metal deactivators, in particular N,N'-disalicylidene-1,2-propane, benzotriazole, EDTA; rust inhibitors, for example carboxylic acids, sulfonates, amines or amine salts; dispersants, e.g. esters, amines of high molecular weight, Mannich bases, succinimides, boronated succinimides; detergents, for example fatty acid amides, non-polymeric amines, polybutene succinimides, polyether amines, low molecular weight amines, sulfonates, salicylic acid derivatives; demulsifiers, for example long-chain alcohols or phenols containing polyethylene or polybutylene groups; antiknock additives, for example manganese methylcyclopentadienyltricarbonyl, oxygen compounds, e.g. esters of vegetable oils, ethers, alcohols for improving the burning behaviour.

Diesel fuels: ignition improvers (cetane improvers), e.g. alkyl nitrates, ether nitrates, alkyl di-glycol nitrates, organic peroxides; stabilisers, in particular for cracked diesel: amines and other N-containing compounds which act as radical interceptors; rust inhibitors, as described above; detergents as described above; oxygen compounds as described above; cold flow improvers, i.e. for example pour point depressants (see above), cloud point depressants or so-called operability additives (OA), which are polymeric multicomponent systems improving, inter alia, the filter flow behaviour.

Preparation process:

The compounds of formulae I and II can be obtained in a manner known per se, for example by reacting a 2-mercaptobenzothiazole of formula

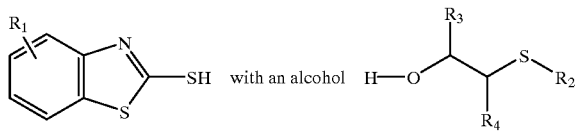

or with a reactive functional derivative thereof, or a 2,5-dimercaptothiadiazole of formula

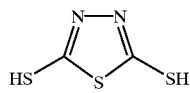

with the alcohol of the above formula or with an alcohol $R_5$—OH or with a reactive functional derivative thereof, with separation of water, preferably under acid conditions.

EXAMPLES

The invention is illustrated by the following Examples. Parts or percentages are by weight, unless otherwise stated.

Example 1

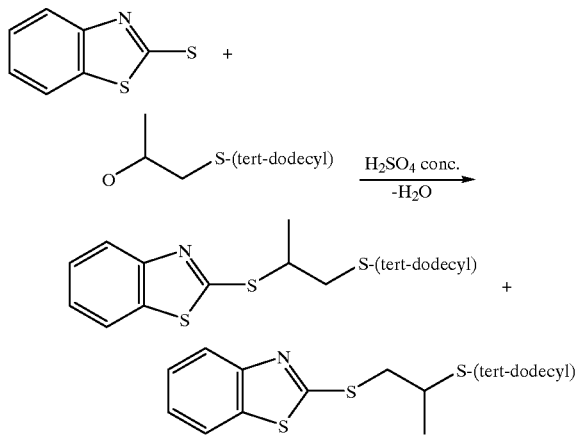

a) 156.3 g (0.6 mol) of the product of Example 1 b) and 1 ml of conc. sulfuric acid are added to a suspension consisting of 105.6 g (0.6 mol) of 2-mercaptobenzothiazole in 800 ml of toluene. This mixture is refluxed in a water separator for 1 hour. The yellow oil is dissolved in 500 ml of hexane and washed with 50 ml of 2N sodium hydroxide solution and water until neutral (pH 7). The organic phase is concentrated by evaporation and the product is dried under reduced pressure (110° C./ c. 0.02 mbar), giving 235 g of a clear, pale yellow oil of medium viscosity (96% of theory).

$n_D^{20}$: 1.5781; elemental analysis: 64.16%; C, (calculated 64.50); 8.62%; H, (calculated 8.61); 4.16%; N, (calculated 3.42); c. 24%; S, (calculated 23.48; problematic determination of S).

b) The starting material is prepared as follows:

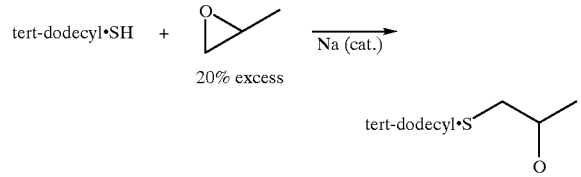

1 g of sodium (~50 mmol) is added to 140 g (2.4 mol) of propylene oxide. Over about 1 hour, 426 g (2 mol) of tert-dodecylmercaptan are added dropwise at 25–30° C. (exothermal course of reaction). The mixture is allowed to react for 1 hour at 55–60° C. and the sodium is deactivated with about 1 ml of acetic acid. The clear, pale yellow crude product is fractionated under reduced pressure (106–110° C./ c. 0.02 mbar), affording 509 g of a clear colourless oil of medium viscosity (98% of theory); $n_D^{20}$: 1.4801.

Example 2

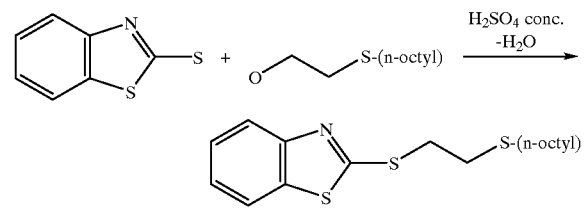

In general analogy to Example 1 a), 16.73 g (0.1 mol) of 2-mercaptobenzothiazole are reacted with 19.03 g (0.1 mol) of 2-(octylthio)ethanol [3547-33-9, Phillips Petroleum, U.S. Pat. No. 2,863,799], affording 33 g of a clear colourless oil (97% of theory).

Elemental analysis: 60.67%; C, (calculated 60.13); 7.40%; H, (calculated 7.42); 3.93%; N (calculated 4.12), c. 27%; S, (calculated 28.32; problematic determination of S).

Example 3

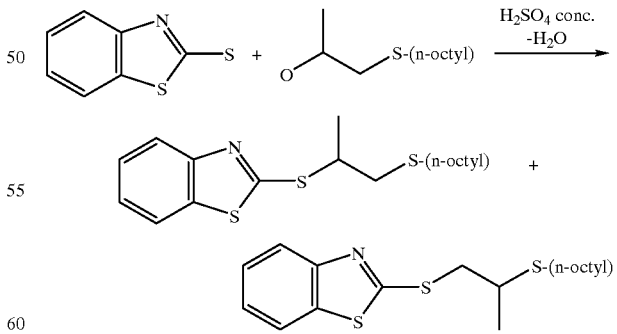

In general analogy to Example 1 a) and Example 2, 16.73 g (0.1 mol) of 2-mercaptobenzothiazole are reacted with 20.43 g (0.1 mol) of 1-octylthio-2-propanol (18915-86-1, Phillips Petroleum, U.S. Pat. No. 2,863,799), affording 32.9 g of an orange-brown oil (93% of theory).

Elemental analysis: 61.29%; C, (calculated 61.14); 7.74%; H, (calculated 7.70); 4.15%; N (calculated 3.96); c. 27%; S, (calculated 27.20; problematic determination of S).

Example 4

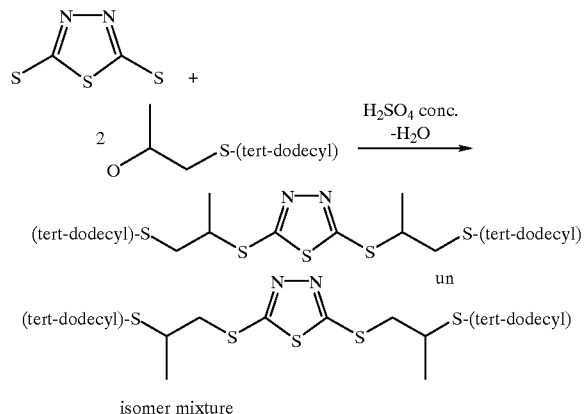

isomer mixture

In general analogy to Example 1 a) and Examples 2 and 3, 60.7 g (0.4 mol) of 2,5-dimercapto-1,3,4-thiadiazole are reacted with 208.4 g (0.8 mol) of the product of Example 1 b, affording 221 g of a clear, pale yellow oil of medium viscosity (87% of theory).

$n_D^{20}$: 1.5488; elemental analysis: 60.35%; C, (calculated 60.51); 9.81%; H, (calculated 9.84); 4.44%; N, (calculated 4.41); c. 25%; S, (calculated 25.24; problematic determination of S).

Example 5

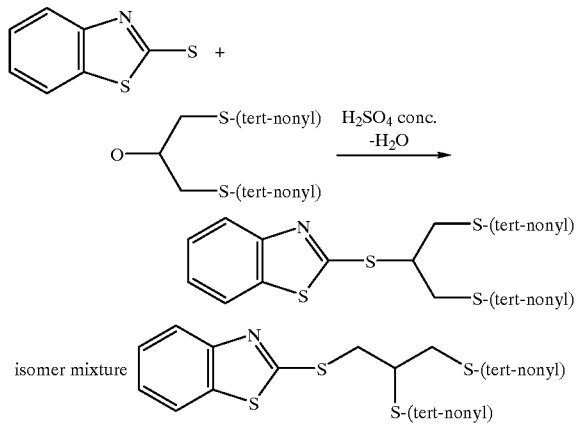

isomer mixture a) In general analogy to Example 1 a) and Examples 2–4, 88 g (0.5 mol) of 2-mercaptobenzothiazole are reacted with 188.5 g (0.5 mol) of the product of Example 5 b), affording 259.7 g of a clear yellow oil of medium viscosity (99% of theory).

$n_D^{20}$: 1.5699; elemental analysis: 64.04%; C, (calculated 63.95); 9.16%; H, (calculated 9.01); 2.70%; N, (calculated 2.66); c. 24.50%; S, (calculated 24.38; problematic determination of S).

b) The starting material is prepared as follows:

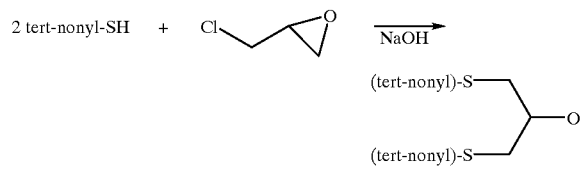

337.5 g (2 mol) of tert-nonylmercaptan and 80 g (2 mol) of sodium hydroxide in 700 ml of ethanol and 320 ml of water are dissolved and homogenised by heating to 50° C. At 25° C., 93.4 g of epichlorohydrin are added dropwise over 1.5 hours. At 60° C., the mixture is allowed to react for 2 hours and the milky emulsion is then concentrated by evaporation. The residue is dissolved with about 100 ml of hexane and washed with 100 ml of water and 3 ml of acetic acid and again with water until neutral (pH 6). The organic phase is concentrated by evaporation and dried under reduced pressure (130° C./ c. 0.03 mbar), giving 378 g of a clear colourless and slightly viscous oil (about 100% of theory).

$n_D^{20}$: 1.4985. Elemental analysis: 67.06%; C, (calculated 66.96); 11.96%; H, (calculated 11.77).

Example 6

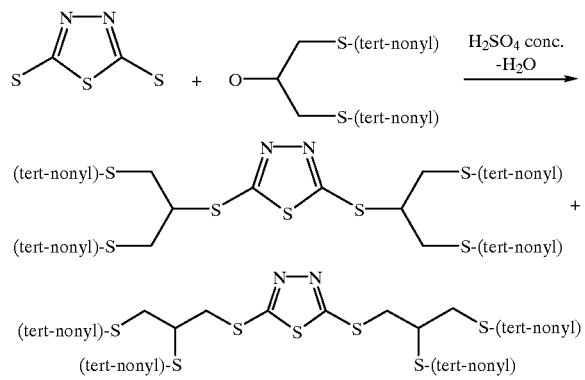

In general analogy to Examples 1 a), 2–4 and 5 a), 105.3 g (0.7 mol) of 2,5-dimercapto-1,3,4-thiadiazole are reacted with 527 g (1.4 mol) of the product of Example 5 b), affording 580 g of a clear, pale yellow oil (95% of theory).

$n_D^2$: 1.5496; elemental analysis: 60.39%; C, (calculated 60.91); 9.91%; H, (calculated 9.99); 3.32%; N, (calculated 3.23); c. 26%; S, (calculated 25.87; problematic determination of S).

Example 7

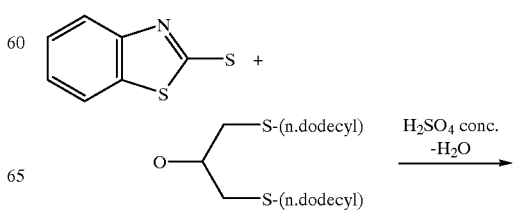

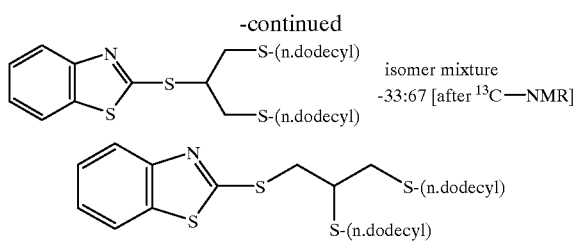

isomer mixture
-33:67 [after $^{13}$C—NMR]

In general analogy to Examples 1 a), 2 . 4, 5 a) and 6, 16.7 g (0.1 mol) of 2-mercaptobenzo-thiazole are reacted with 46.1 g (0.1 mol) of 1,3-bis(dodecylthio)-2-propanol [59852-53-8, U.S. Pat. No. 3,954,839], affording 59.6 g of an orange-brown oil (98% of theory).

Elemental analysis: 67.06%; C, (calculated 66.94); 9.86%; H, (calculated 9.75); 2.10%; N, (calculated 2.30); 21%; S, (calculated 21.02).

Example 8

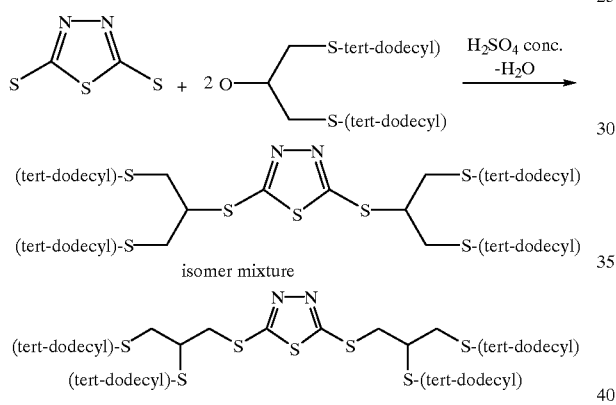

a) In general analogy to Examples 1 a), 2–4, 5 a), 6 and 7, 38 g (0.25 mol) of 2,5-dimercapto-1,3,4-thiadiazole are reacted with 230.45 g (0.5 mol) of the product of Example 8 b), giving 244 g of a clear, pale yellow oil of medium viscosity (94% of theory).

$n_D^{20}$: 1.5396; elemental analysis: 64.04%; C, (calculated 64.93); 10.63%; H, (calculated 10.70); 2.93%; N, (calculated 2.70); c. 22%; S, (calculated 21.66; problematic determination of S).

b) The starting material is prepared as follows:

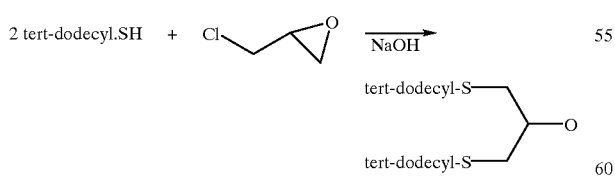

In general analogy to Example 8 b), 426 g (2 mol) of tert-dodecylmercaptan are reacted with 93.5 g (1 mol) of epichlorohydrin and 80 g (2 mol) of sodium hydroxide, affording 460 g of a clear colourless oil of medium viscosity (99% of theory). $n_D^{20}$: 1.4956.

Example 9

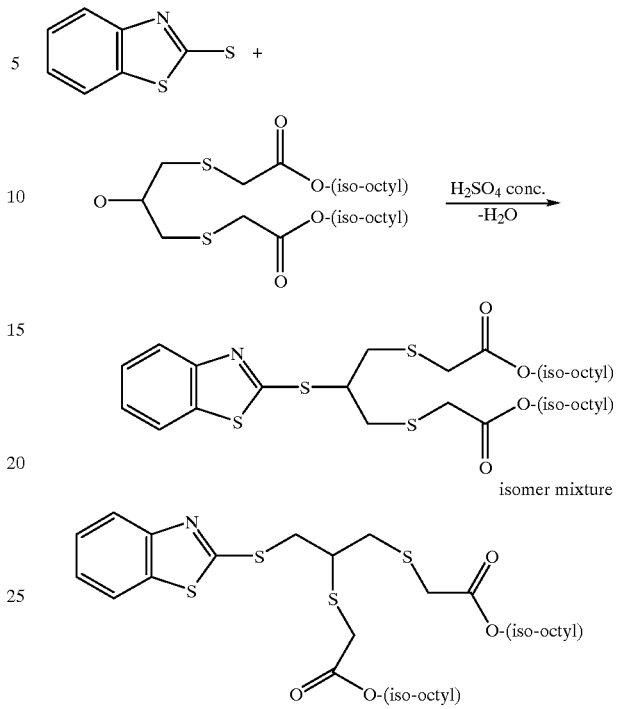

a) In general analogy to Examples 1a), 2–4, 5a), 6, 7 and 8a), 8.8 g (0.05 mol) of 2-mercaptobenzothiazole are reacted with 23.2 g (0.05 mol) of the product of Example 9b). 26 g of crude product are purified by column chromatography over 200 g of silica gel (toluene/ethyl acetate), giving 10.7 g of a clear, pale yellow oil of medium viscosity. $n_D^{20}$: 1.5534. Elemental analysis: 58.48; C, (calculated 58.69); 7.82%; H, (calculated 7.72); 2.44%; N, (calculated 2.28); c. 21%; S, (calculated 20.89, problematic determination of S).

b) Preparation of the starting material:

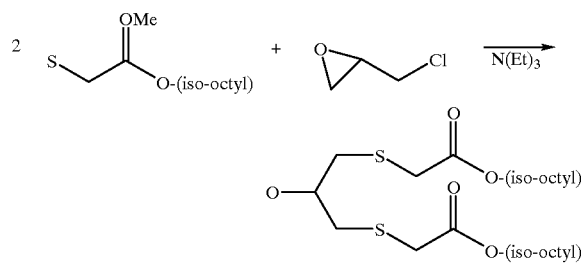

9.4 g (0.1 mol) of epichlorohydrin are added dropwise over 30 min to 40.8 g (0.2 mol) of iso-octyl 2-mercaptoacetate* and 21.2 g (0.211 mol) of triethylamine in 100 ml of toluene. This mixture is then stirred for 12 hours at 60–110° C. The product, concentrated by evaporation, is dissolved in 100 ml of ethyl acetate and is then washed with 100 ml water (+some 2N HCl) and concentrated again by evaporation. Some (c. 11 g) unreacted educt (IOMA*) is distilled off under reduced pressure (75–85° C./c. 0.03 mbar), giving as main product 34.3 g of a clear colourless oil of medium viscosity (74% of theory).

Elemental analysis: 57.22%; C, (calculated 59.45); 9.31%; H, (calculated 9.54); c. 13%; S, (calculated 13.80, problematic determination of S).

*) thioglycol acid ester of branched-chain octanols (IOMA)

Example 10

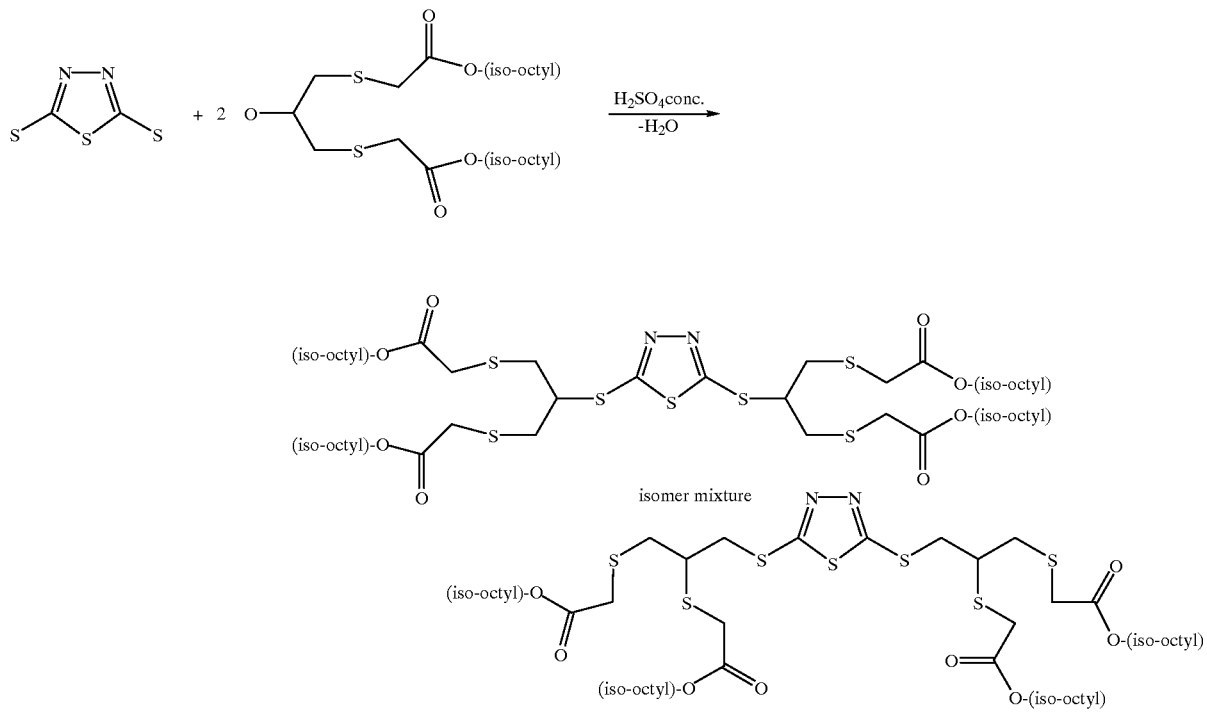

In general analogy to Examples 1a), 2–4, 5a), 6, 7, 8 a) and 9 a), 7.6 g (0.05 mol) of 2,5-dimercapto-1,3,4-thiadiazole are reacted with 46.5 g (0.1 mol) of the product of Example 9b). 48 g of crude product are purified by column chromatography over 300 g of silica gel (toluene/ethyl acetate), giving 22 g of a clear yellow oil of medium viscosity.

$n_D^{20}$: 1.5224; elemental analysis: 55.88; C, (calculated 55.24); 8.70%; H, (calculated 8.31); 2.32%; N, (calculated 2.68); c. 20%; S, (calculated 21.55; problematic determination of S).

Example 11 a) In general analogy to Example 1a), 123 g (0.7 mol) of 2-mercaptobenzothiazole are reacted with 203 g (0.7 mol) of the product of Example 11b), affording 299 g of a yellow oil of medium viscosity (97% of theory).
$n_D^{20}$ 1.5682; elemental analysis: 62.90%; C, (calculated 62.82); 8.57%; H, (calculated 8.48); 3.33%; N, (calculated 3.19); 21.97%; S, (calculated 21.87).

b) The starting material is prepared as follows:

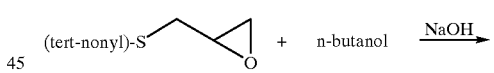

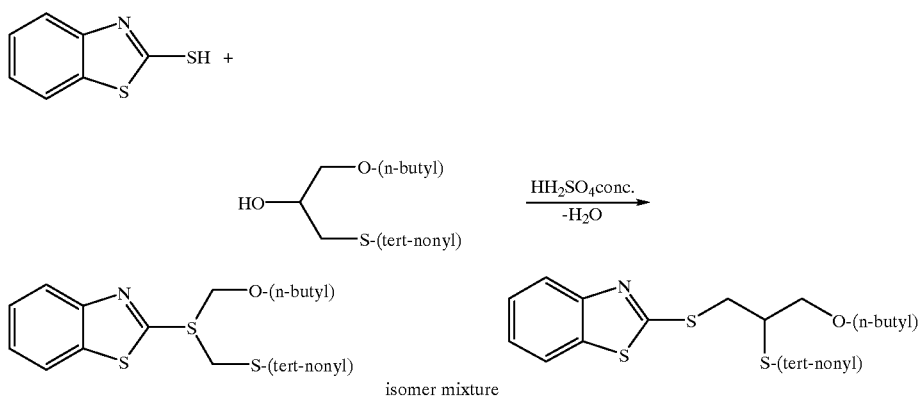

-continued

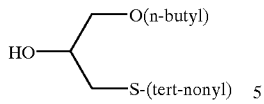

433 g (2 mol) of tert-nonyl-glycidyl thioether [for the preparation thereof see U.S. Pat. No. 4,931,5761] are added to a solution consisting of 40 g (1 mol) of sodium hydroxide in 3 l of n-butanol over 15 min at 60–65° C. This mixture is stirred for 4 hours at about 60° C. and excess n-butanol is removed by distillation. After addition of 300 ml of special-boiling point spirit (b.p. 60–90° C.), the product is washed with dilute hydrochloric acid until neutral. Concentrating the organic phase by evaporation and then drying the product under reduced pressure (120° C. /0.05 mbar) gives 564 g of a clear yellow oil of medium viscosity (97% of theory). $n_D^{20}$ 1.4756; elemental analysis: 66.15%; C, (calculated 66.15); 11.76%; H, (calculated 11.80); 11.30%; S, (calculated 11.04).

Example 12

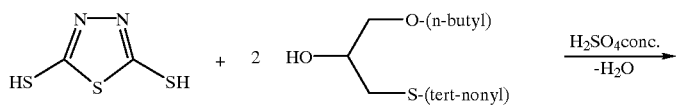

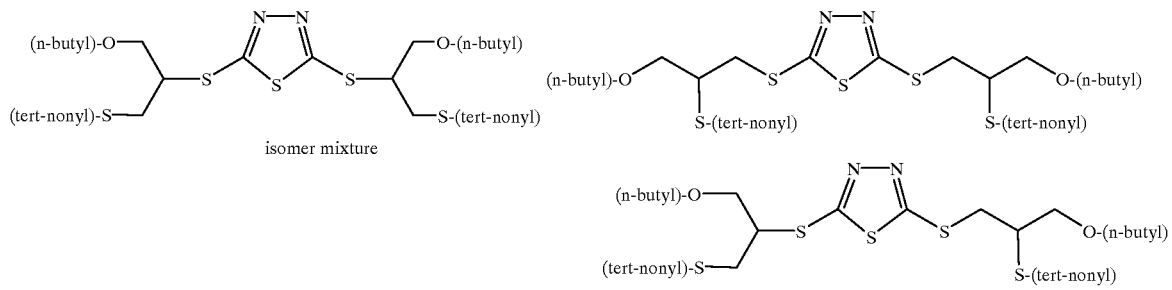

In general analogy to Example 1a) 60 g (0.4 mmol) 2,5-dimercapto-1,3,4-thiadiazole are reacted with 232 g (0.8 mmol) of the product of Example 11b) affording 265 g, of a clear yellow oil of medium viscosity (95% of theory).

$n_D^{20}$ 1.5364; elemental analysis: 58.48%; C, (calculated 58.75); 9.75%; H, (calculated 9.57); 4.12%; N, (calculated 4.03); 23.23%; S, (calculated 23.06).

Example 13

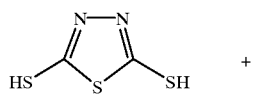

+

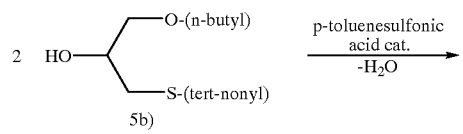

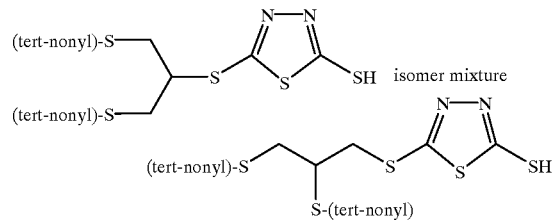

75 g (0.5 mol) of 2,5-dimercapto-1,3,4-thiadiazole and 4.8 g (5 mol %) of p-toluenesulfonic acid are added to a solution consisting of 188 g (0.5 mol) of the product of Example 5b) in 600 ml of toluene. This mixture is refluxed for 1 hour in a water separator and the toluene is then removed by distillation. The crude product is dissolved in 300 ml of special-boiling point spirit (b.p. 60–90° C.), washed until neutral, concentrated by evaporation and dried under reduced pressure (110° C./0.05 mbar, 30 min.), giving 244 g of a clear yellow viscous oil which has a slightly unpleasant smell (96% of theory).

$n_D^{20}$ 1.5834; elemental analysis: 54.33%; C, (calculated 54.28); 8.73%; H, (calculated 8.71); 5.66%; N, (calculated 5.50); 32.32%; S, (calculated 31.50).

Example 14

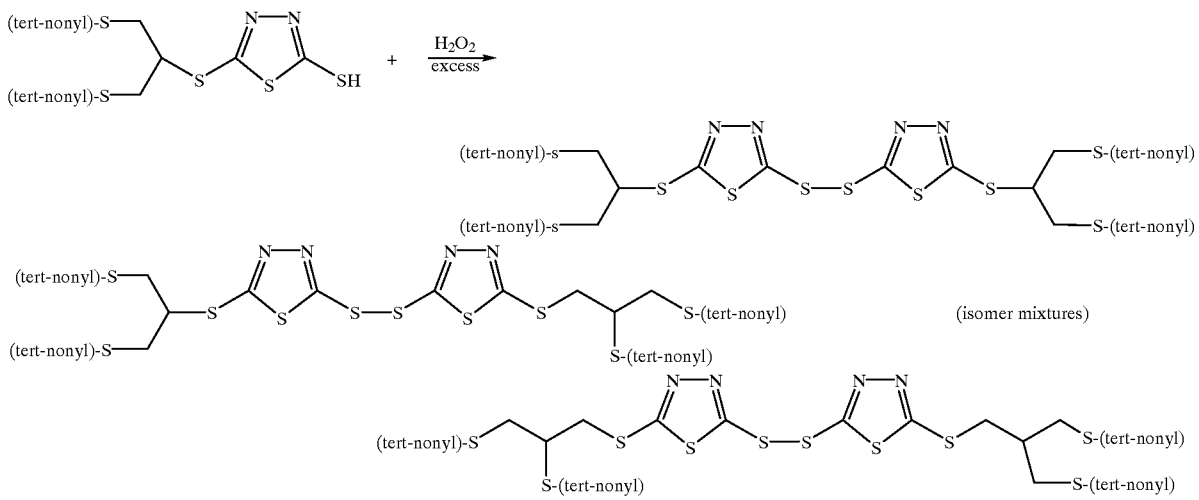

A solution consisting of 104 g of hydrogen peroxide 15% (0.5 mol) is added dropwise over 30 min at about 30° C. to a solution consisting of 254 g (0.5 mol) of the product of Example 13 in 250 ml of acetone. This mixture is stirred for 1 hour at 50° C. and is then charged at room temperature with sodium hydrogen sulfite solution (39%) until peroxide can no longer be detected. The acetone is then removed by distillation and the crude product is dissolved in 300 ml of special-boiling point spirit (b.p. 60–90° C.), washed with water, concentrated by evaporation and dried under reduced pressure (100° C./0.04 mbar, 30 min.), giving 234 g of a clear, viscous, yellow oil (92% of theory).

$n_D^{20}$ 1.5810; elemental analysis: 54.16%; C, (calculated 54.39); 8.49%; H, (calculated 8.53); 5.45%; N, (calculated 5.52); 31.51%; S, (calculated 31.56).

Example 15

Antiwear test: To test the suitability as antiwear additive, the ASTM standard method D-2783-81 is applied using a Shell four-ball tester. The base oil used is Stock 305, of Mobil, to which the compound according to the respective Example cited is added in the amount indicated in Table I. The average wear scar diameter WSD (in mm) is determined at a 40 kg and at 1440 rpm after 1 hour of operation at 100° C. The results obtained are compiled in Table I.

TABLE

| Compound of Example | Additive amount [% by weight] | WSD [mm] |
|---|---|---|
| base oil | — | 2.32 |
| 1 | 1.0 | 0.78 |
| 4 | 1.0 | 0.78 |
| 5 | 1.0 | 0.71 |
| 6 | 1.0 | 0.83 |
| 8 | 1.0 | 0.77 |
| 9 | 1.0 | 0.78 |
| 11 | 1.0 | 0.78 |

What is claimed is:

1. A compound of the formula

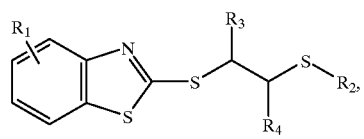

(I)

wherein

R. is hydrogen or $C_1$–$C_{20}$alkyl;

$R_2$ is a substituent selected from the group consisting of $C_5$–$C_{12}$cycloalkyl and $C_7$–$C_{12}$bicycloalkyl, which substituents are substituted by one or more than one substituents selected from the group consisting of amino, carboxy and hydroxy; or is $C_3$–$C_{20}$alkyl which is interrupted by one or more than one bivalent radicals selected from the group consisting of —O—, —$NR_6$—, —C(=O)—O—, —O—C(=O)—, —C(=O)—$NR_6$— and —$NR_6$—C(=O)—;

$R_3$ and $R_4$ are substituents selected from the group consisting of $C_5$–$C_{12}$cycloalkyl, $C_7$–$C_{12}$bicycloalkyl, phenyl, $C_7$–$C_{18}$alkylphenyl, naphthyl and $C_7$–$C_9$phenylalkyl which substituents may be substituted by one or more than one substituents selected from the group consisting of amino, carboxy and hydroxy; $C_1$–$C_{20}$alkyl or $C_3$–$C_{20}$alkyl which is interrupted by one or more than one bivalent radicals selected from the group consisting of —O—, —$NR_6$—, —C(=O)—O—, —O—C(=O)—, —C(=O)—$NR_6$— and —$NR_6$—C(=O)—; and $R_6$ is hydrogen or $C_1$–$C_4$alkyl.

2. A compound of the formula (I) according to claim 1, wherein $R_1$ is hydrogen;

$R_2$ is $C_3$–$C_{20}$alkyl which is interrupted by one or more than one bivalent radicals selected from the group consisting of —O—, —$NR_6$—, —C(=O)—O—, —O—C(=O)—, —C(=O)—$NR_6$— and —$NR_6$—C(=O)—;

$R_3$ and $R_4$ are $C_1$–$C_{20}$alkyl or $C_3$–$C_{20}$alkyl which is interrupted by one or more than one bivalent radicals selected from the group consisting of —O—, —NR$_6$—, —C(=O)—O—, —O—C(=O)—, —C(=O)—NR$_6$— and —NR$_6$—C(=O)—; and R$_6$ is hydrogen or C$_1$–C$_4$alkyl.

3. A compound of the formula (I) according to claim 1, wherein

R$_1$ is hydrogen;

R$_2$ is C$_3$–C$_{20}$alkyl which is interrupted by one or more than one bivalent radicals selected from the group consisting of —O—, —C(=O)—O— and —O—C(=O)—; and R$_3$ and R$_4$ are C$_1$–C$_{20}$alkyl or C$_3$–C$_{20}$alkyl which is interrupted by one or more than one bivalent radicals selected from the group consisting of —O—, —C(=O)—O— and —O—C(=O)—.

4. A composition which comprises a compound of the formula (I) according to claim 1 or mixtures thereof in combination with a base oil of lubricating viscosity.

5. A compound of the formula

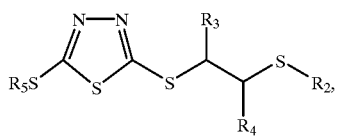

(II)

wherein

R$_2$ is a substituent selected from the group consisting of C$_5$–C$_{12}$cycloalkyl, C$_7$–C$_{12}$bicycloalkyl, phenyl, C$_7$–C$_{18}$alkylphenyl, naphthyl and C$_7$–C$_9$phenylalkyl which substituents may be substituted by one or more than one substituents selected from the group consisting of amino, carboxy and hydroxy; C$_1$–C$_{20}$alkyl or is C$_3$–C$_{20}$alkyl which is interrupted by one or more than one bivalent radicals selected from the group consisting of —O—, —NR$_6$—, —C(=O)—O—, —O—C(=O)—, —C(=O)—NR$_6$— and —NR$_6$—C(=O)—;

R$_3$ and R$_4$ are hydrogen or have the meanings of R$_2$ with the proviso that R$_2$ is C$_4$–C$_{20}$alkyl if R$_3$ and R$_4$ are hydrogen;

R$_5$ is hydrogen or represents a group of the partial formulae

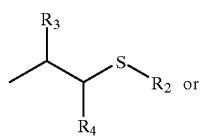

(A)

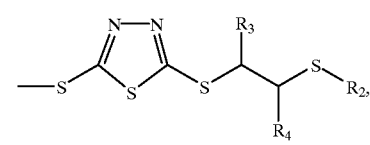

(B)

wherein

R$_2$, R$_3$ and R$_4$ have the meanings of above; and

R$_6$ is hydrogen or C$_1$–C$_4$alkyl.

6. A compound of the formula (II) according to claim 5, wherein

R$_2$ is a substituent selected from the group consisting of phenyl, C$_7$–C$_{18}$alkylphenyl and C$_7$–C$_9$phenylalkyl which substituent may be substituted by one or more than one substituents selected from the group consisting of amino, carboxy and hydroxy; C$_1$–C$_{20}$alkyl or is C$_3$–C$_{20}$alkyl which is interrupted by one or more than one bivalent radicals selected from the group consisting of —O—, —NR$_6$—, —C(=O)—O—, —O—C(=O)—, —C(=O)—NR$_6$— and —NR$_6$—C(=O)—;

R$_3$ and R$_4$ are hydrogen or have the meanings of R$_2$ with the proviso that R$_2$ is C$_4$–C$_{20}$alkyl if R$_3$ and R$_4$ are hydrogen;

R$_5$ is hydrogen or represents a group of the partial formulae (A) and (B), wherein R$_2$, R$_3$ and R$_4$ have the meanings of above; and R$_6$ is hydrogen or C$_1$–C$_4$alkyl.

7. A compound of the formula (II) according to claim 5, wherein

R$_1$ is hydrogen;

R$_2$ is a substituent selected from the group consisting of phenyl, C$_7$–C$_{18}$alkylphenyl and C$_7$–C$_9$phenylalkyl; C$_1$–C$_{20}$alkyl or is C$_3$–C$_{20}$alkyl which substituent may be interrupted by one or more than one bivalent radicals selected from the group consisting of —O—, —C(=O)—O— and —O—C(=O)—; and R$_3$ and R$_4$ are hydrogen or have the meanings of R$_2$ with the proviso that R$_2$ is C$_4$–C$_{20}$alkyl if R$_3$ and R$_4$ are hydrogen;

R$_5$ is hydrogen or represents a group of the partial formulae (A) and (B), wherein R$_2$, R$_3$ and R$_4$ have the meanings of above.

8. A composition which comprises a compound of the formula (II) according to claim 5 or mixtures thereof in combination with a base oil of lubricating viscosity.

9. A compound of the formula

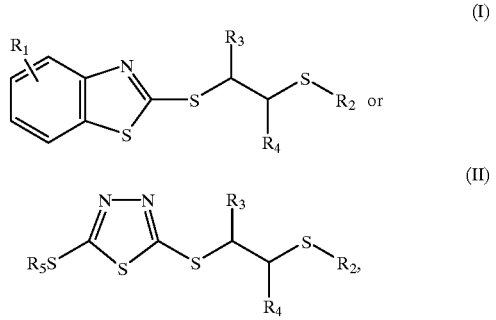

wherein

R$_1$ is hydrogen;

R$_2$ is C$_3$–C$_{20}$alkyl which is interrupted by one or more than one bivalent radicals selected from the group consisting of —O—, —C(=O)—O— and —O—C(=O)—; and one of R$_3$ and R$_4$ is hydrogen and the other one is C$_1$–C$_{20}$alkyl or has the meanings of R$_2$; or R$_3$ and R$_4$ are C$_1$–C$_{20}$alkyl or have the meanings of R$_2$;

R$_5$ is C$_3$–C$_{20}$ alkyl which is interrupted by one or more than one bivalent radicals selected from the group consisting of —O—, —C(=O)—O— and —O—C(=O)—; or represents a group of the partial formulae (A)

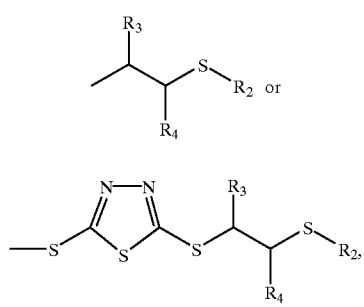

(B)

wherein

R$_2$, R$_3$ and R$_4$ have the meanings of above.

10. A method of lubricating a combustion engine, which comprises lubricating said engine with a lubricant comprising at least one compound of the formula

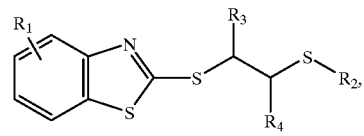
(I)

wherein

R$_1$ is hydrogen or C$_1$–C$_{20}$alkyl;

R$_2$ is a substituent selected from the group consisting of C$_5$–C$_{12}$cycloalkyl, C$_7$–C$_{12}$bicycloalkyl, phenyl, C$_7$–C$_{18}$alkylphenyl, naphthyl and C$_7$–C$_9$phenylalkyl which substituent may be substituted by one or more than one substituents selected from the group consisting of amino, carboxy and hydroxy; C$_1$–C$_{20}$alkyl or is C$_3$–C$_{20}$alkyl which is interrupted by one or more than one bivalent radicals selected from the group consisting of —O—, —NR$_6$—, —C(=O)—O—, —O—C(=O)—, —C(=O)—NR$_6$— and —NR$_6$—C(=O)—;

R$_3$ and R$_4$ are hydrogen or have the meanings of R$_2$, with the proviso that R$_2$ is C$_4$–C$_{20}$alkyl if R$_3$ and R$_4$ is hydrogen; and R$_6$ is hydrogen or C$_1$–C$_4$alkyl.

11. A method of lubricating metals, which comprises lubricating metals with a metal working fluid comprising at least one compound of the formula

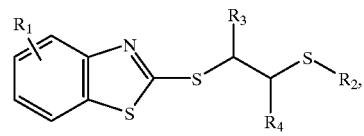
(I)

wherein

R$_1$–R$_4$ are as defined in claim 10.

12. A method for improving the performance properties of lubricants, which comprises adding to a base oil of lubricating viscosity at least one compound of the formula

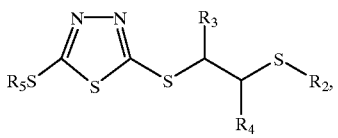
(II)

wherein

R$_2$ is a substituent selected from the group consisting of C$_5$–C$_{12}$cycloalkyl, C$_7$–C$_{12}$bicycloalkyl, phenyl, C$_7$–C$_{18}$alkylphenyl, naphthyl and C$_7$–C$_9$phenylalkyl which substituent may be substituted by one or more than one substituents selected from the group consisting of amino, carboxy and hydroxy; C$_1$–C$_{20}$alkyl or is C$_3$–C$_{20}$alkyl which is interrupted by one or more than one bivalent radicals selected from the group consisting of —O—, —NR$_6$—, —C(=O)—O—, —O—C(=O)—, —C(=O)—NR$_6$— and —NR$_6$—C(=O)—;

R$_3$ and R$_4$ are hydrogen or have the meanings of R$_2$, with the proviso that R$_2$ is C$_4$–C$_{20}$alkyl if R$_3$ and R$_4$ is hydrogen;

R$_5$ is hydrogen or represents a group of the partial formulae

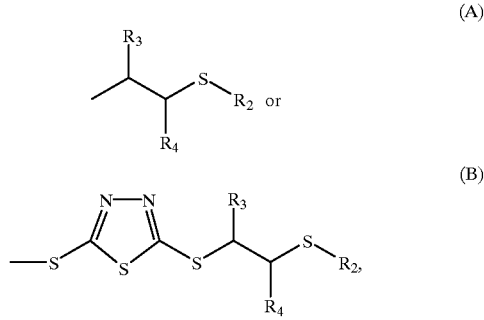

(A)

(B)

wherein

R$_2$, R$_3$ and R$_4$ have the meanings of above; and

R$_6$ is hydrogen or C$_1$–C$_4$alkyl.

* * * * *